(12) United States Patent
Southard, Jr.

(10) Patent No.: US 10,398,731 B2
(45) Date of Patent: Sep. 3, 2019

(54) TREATMENT FOR WARTS

(71) Applicant: James H Southard, Jr., Charleston, SC (US)

(72) Inventor: James H Southard, Jr., Charleston, SC (US)

(*) Notice: Subject to any disclaimer, the term of this patent is extended or adjusted under 35 U.S.C. 154(b) by 0 days.

(21) Appl. No.: 15/619,704

(22) Filed: Jun. 12, 2017

(65) Prior Publication Data
US 2018/0353537 A1 Dec. 13, 2018

(51) Int. Cl.
*A61K 33/24* (2019.01)
*A61K 9/00* (2006.01)
*A61K 47/08* (2006.01)
*A61K 36/61* (2006.01)
*A61K 45/06* (2006.01)
*A61K 47/02* (2006.01)
*A61K 9/06* (2006.01)
*A61K 47/46* (2006.01)
*A61K 9/70* (2006.01)
*A61F 13/00* (2006.01)

(52) U.S. Cl.
CPC ............ *A61K 33/24* (2013.01); *A61K 9/0014* (2013.01); *A61K 9/06* (2013.01); *A61K 9/70* (2013.01); *A61K 36/61* (2013.01); *A61K 45/06* (2013.01); *A61K 47/02* (2013.01); *A61K 47/08* (2013.01); *A61K 47/46* (2013.01); *A61F 2013/00506* (2013.01)

(58) Field of Classification Search
CPC . A61F 2013/506; A61K 33/24; A61K 9/0014; A61K 45/06
USPC .......................................................... 424/627
See application file for complete search history.

(56) References Cited

U.S. PATENT DOCUMENTS

| 4,661,354 A | 4/1987 | Finnerty |
| 6,344,190 B1 | 2/2002 | Nair et al. |
| 2008/0253973 A1* | 10/2008 | Tamarkin ............... A61K 8/046 424/47 |
| 2015/0290042 A1* | 10/2015 | Freer ................... A61F 13/0213 602/43 |

FOREIGN PATENT DOCUMENTS

| CN | 101057953 A | * 10/2007 |
| CN | 201410093707 | 5/2014 |
| WO | 2007139812 | 12/2007 |

OTHER PUBLICATIONS

Stefani et al., Efficacy Comparison Between Cimetine and Zinc Sulphate in Treatment of Multiple and Recalicitrant Warts, Anas. Bras. Dermetol., vol. 84, No. 1, Rio De Janero Jan./Feb. 2009.

* cited by examiner

*Primary Examiner* — Yanzhi Zhang
(74) *Attorney, Agent, or Firm* — Moore, Ingram, Johnson & Steele, LLP

(57) ABSTRACT

The present invention relates to the treatment of warts using a transition metal, plated transition metal or transition metal alloy and an ointment containing Camphor, Menthol and *Eucalyptus* Oil.

9 Claims, 1 Drawing Sheet

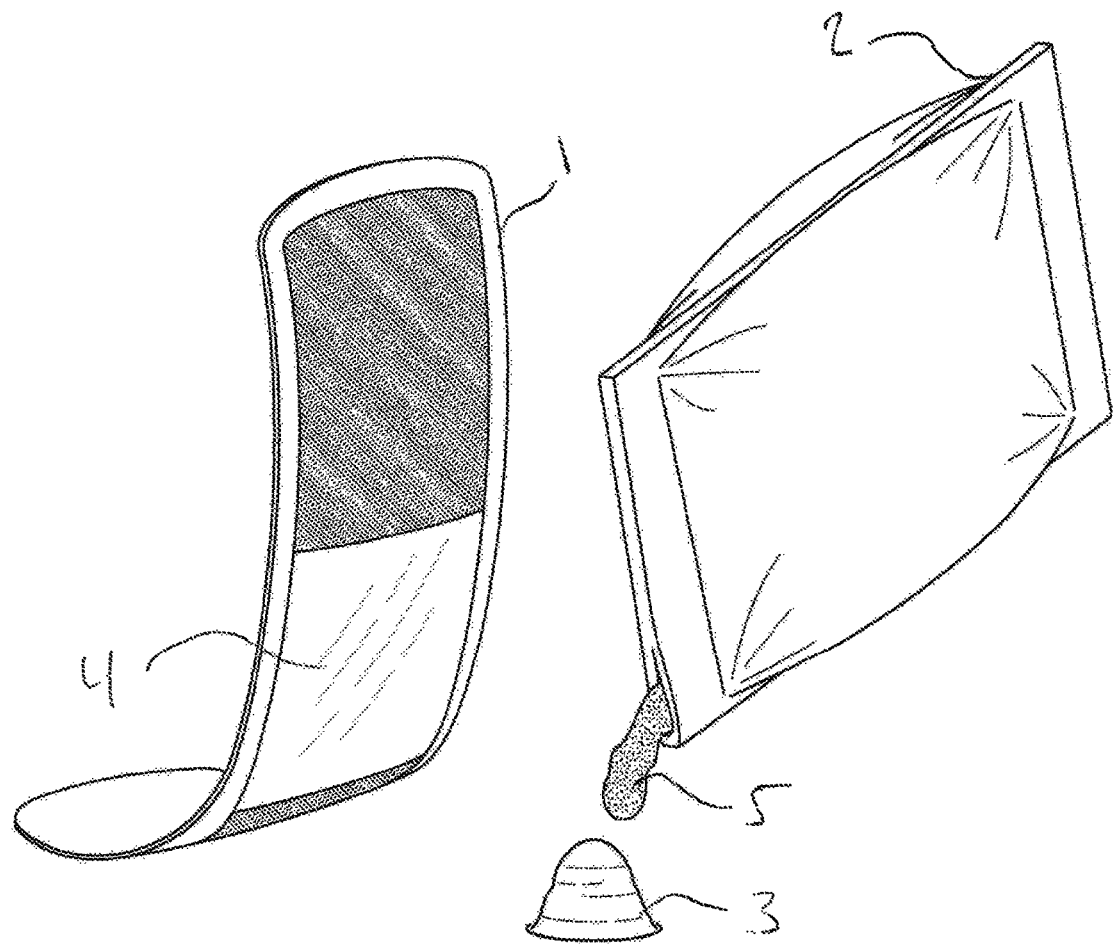

TREATMENT FOR WARTS

FIELD OF THE INVENTION

The present invention relates to the treatment of warts using a transition metal, plated transition metal or transition metal alloy and an ointment containing Camphor, Menthol and *Eucalyptus* Oil.

BACKGROUND OF THE INVENTION

Warts are notoriously difficult to remove and often freezing is expensive and ineffective. Alternative treatments often include expensive physician intervention or prolonged treatment with salicylic acid. An effective, easy and cost-effective remedy is needed.

SUMMARY OF THE INVENTION

The present invention provides a safe, effective and easy to use wart treatment for human and veterinary populations. The warts to be treated include, but are not limited to common warts and plantar warts. The preferred embodiment of the present invention comprises a kit further comprising a metal and a container comprising an ointment. The metal of the present invention comprises a sheet or flat piece of a transition metal, a plated transition metal such as copper-plated zinc, or transition metal alloy.

In a preferred embodiment the ointment is deposited on the wart and the metal sheet is placed over the ointment. A bandage is then used to hold the metal and ointment in place over the wart. The bandage and ointment are replaced daily as needed. The treatment of the present invention comprises the ointment and the metal. In a preferred embodiment, the treatment further comprises at least one bandage, at least one metal sheet sized to fit beneath the bandage and ointment. In a further embodiment, the metal ointment and bandage are supplied together in a treatment kit.

BRIEF DESCRIPTION OF THE DRAWINGS

FIG. 1 is a schematic of an embodiment of the invention showing the ointment and the bandage with the metal in use to treat a wart.

DETAILED DESCRIPTION OF THE INVENTION

FIG. 1 is a schematic representation of a preferred embodiment of a kit 6 (not shown) of the present invention that has been opened, and is used to treat a wart 3. In the preferred embodiment shown in FIG. 1, the kit comprises a bandage 1, further comprising a metal 4, and an ointment container 2. The ointment 5, is deposited on the wart 3 then covered with the metal 4 and bandage 1.

In the preferred embodiment of FIG. 1, the metal 4 is a thin sheet of a metal and is attached to the bandage 1. In further embodiments, the metal 4 may be separate from bandage 1. The metal 4 may be of any shape or size in relation to bandage 1.

The metal 4, is preferably a copper-zinc combination (5-97.5% zinc, 2.5%-95% copper). The copper-zinc combination is preferably copper-plated zinc (50% zinc, 50% copper), more preferably (97.5% zinc, 2.5% copper). Further embodiments include, but are not limited to copper-plated zinc (99.2% zinc, 0.8% copper), a copper-zinc alloy (5-97.5% zinc, 2.5%-95% copper, more preferably 95% copper, 5% zinc), and solid zinc or copper sheets. Alternative embodiments include other transition metal alloys, plated transition metals and transition metal sheets.

In a preferred embodiment, the ointment 5 is comprised of ingredients including camphor and/or a similar ingredient such as menthol and *eucalyptus* oil. In a further embodiment alternative terpenoids may be used in place of camphor. The ointment is preferably 0-100% camphor and 0-100% *eucalyptus* oil, more preferably 0-10% camphor and 0-10% *eucalyptus* oil, most preferably 4.8% camphor and 1.2% *eucalyptus* oil. In a further embodiment, the ointment preferably comprises 0-100% menthol, more preferably 0.1-10% menthol, most preferably 2.6% menthol in addition to or in place of the camphor. The ointment 5 may further comprise ingredients such as oils and fragrance.

In a further embodiment, the ointment container 2 is a single use packet or tube. In this embodiment, the kit 6 comprises multiple single-use packets of ointment 5. In a further embodiment, the ointment container 2 is a multi-use packet or tube that dispenses ointment and is re-capped or sealed after each use.

In a preferred embodiment, the kit 6 comprises at least one bandage 1. Bandage 1 preferably comprises a flexible adhesive strip to hold the metal 4 and ointment 5 in place over the wart 3. In a preferred embodiment, the metal 4 is attached to the bandage 1 for ease of use. In a further embodiment, the bandage 1 may be flexible or inflexible gauze that requires a hook, latch or tape to remain in place.

I claim:

1. A composition for the treatment of a wart comprising:
   a thin sheet of a metal, and
   an ointment, wherein the metal is a Copper-Zinc alloy comprising 5-97.5% Zinc and 2.5%-95% Copper, wherein the ointment is placed in direct contact with the wart and the thin sheet of metal is then placed in direct contact with the ointment.

2. The treatment of claim 1 wherein the ointment comprises 0.1-10% Camphor.

3. The treatment of claim 1 wherein the ointment comprises 0.1-10% Menthol.

4. The treatment of claim 1 wherein the ointment comprises Camphor, *Eucalyptus* Oil, and Menthol.

5. A composition for the treatment of warts comprising:
   a thin sheet of a metal, and
   an ointment,
   wherein the metal is Copper-plated Zinc comprising 50%-99.2% Zinc and 0.8%-50% Copper.

6. The treatment of claim 5 wherein the ointment comprises 0.01-10% Camphor.

7. The treatment of claim 5 wherein the ointment comprises 0.01-10% Menthol.

8. The treatment of claim 5 wherein the ointment comprises Camphor, *Eucalyptus* Oil, and Menthol.

9. A composition for the treatment of warts comprising:
   a thin sheet of a metal, and
   an ointment,
   wherein the metal is Copper-plated Zinc comprising 97.5% Zinc and 2.5% Copper and the ointment comprises 4-5% Camphor, 1-2% *Eucalyptus* Oil, and 2-3% Menthol.

* * * * *